United States Patent
Goetzl

(10) Patent No.: US 11,360,097 B2
(45) Date of Patent: Jun. 14, 2022

(54) PLATELET BIOMARKERS AND DIAGNOSTIC METHODS FOR VASCULAR DISEASES

(71) Applicant: Edward J Goetzl, San Francisco, CA (US)

(72) Inventor: Edward J Goetzl, San Francisco, CA (US)

( * ) Notice: Subject to any disclaimer, the term of this patent is extended or adjusted under 35 U.S.C. 154(b) by 203 days.

(21) Appl. No.: 15/775,788

(22) PCT Filed: Nov. 11, 2016

(86) PCT No.: PCT/US2016/061452
§ 371 (c)(1),
(2) Date: May 11, 2018

(87) PCT Pub. No.: WO2017/083599
PCT Pub. Date: May 18, 2017

(65) Prior Publication Data
US 2018/0328940 A1    Nov. 15, 2018

Related U.S. Application Data

(60) Provisional application No. 62/295,396, filed on Feb. 15, 2016, provisional application No. 62/254,184, filed on Nov. 12, 2015.

(51) Int. Cl.
| | |
|---|---|
| *G01N 33/68* | (2006.01) |
| *C07K 16/18* | (2006.01) |
| *C07K 14/47* | (2006.01) |
| *G01N 33/53* | (2006.01) |
| *G01N 33/86* | (2006.01) |
| *G01N 1/40* | (2006.01) |
| *C12N 5/078* | (2010.01) |
| *A61P 7/02* | (2006.01) |
| *A61K 9/127* | (2006.01) |

(52) U.S. Cl.
CPC ......... *G01N 33/6842* (2013.01); *A61K 9/127* (2013.01); *A61P 7/02* (2018.01); *C07K 14/47* (2013.01); *C07K 16/18* (2013.01); *C12N 5/0644* (2013.01); *G01N 1/40* (2013.01); *G01N 33/5308* (2013.01); *G01N 33/86* (2013.01); *G01N 2333/475* (2013.01); *G01N 2333/521* (2013.01); *G01N 2333/70564* (2013.01); *G01N 2333/745* (2013.01); *G01N 2333/916* (2013.01); *G01N 2400/00* (2013.01); *G01N 2800/2871* (2013.01); *G01N 2800/32* (2013.01)

(58) Field of Classification Search
None
See application file for complete search history.

(56) References Cited

U.S. PATENT DOCUMENTS

| | | | |
|---|---|---|---|
| 2013/0178383 A1* | 7/2013 | Spetzler | G01N 1/4077 506/9 |
| 2015/0119278 A1 | 4/2015 | Goetzl | |
| 2015/0306212 A1 | 10/2015 | Kahvejian et al. | |

FOREIGN PATENT DOCUMENTS

WO    WO 2013/149859 A1    10/2013

OTHER PUBLICATIONS

Flaumenhaft et al., Elected species Megakaryocyte-derived microparticles: direct visualization and distinction from platelet-derived microparticles, Blood, 2009, 113(5), 1112-1121. (Year: 2009).*
Abner et al. "Plasma Neuronal Exosomal Levels of Alzheimer's Disease Biomarkers in Normal Aging," Annals of Clinical and Translational Neurology, May 1, 2016 (May 1, 2016) vol. 3, pp. 399-403.
Goetzl et al. "Human PLasma PLatelet-Derived Exosomes: Effects of Aspirin" The FASEB Journal, May 1, 2016 (May 1, 2016), vol. 30, pp. 2058-2063. entire document.
Kapur et al. "Nouvelle Cuisine: Platelets Served with Inflammation," The Journal of Immunology, Jun. 15, 2015 (Jun. 15, 2015), vol. 194, pp. 5579-5587. entire document.

* cited by examiner

*Primary Examiner* — Changhwa J Cheu
(74) *Attorney, Agent, or Firm* — Law Office of Chistopher Jacob, P.C.

(57) ABSTRACT

The present invention relates to biomarkers and diagnostic and prognostic methods for vascular diseases. In particular, proteins of platelet-derived exosomes have been identified as biomarkers that can be used to detect platelet activation associated with pathogenesis of vascular diseases, including cardiovascular and cerebrovascular diseases. The invention also provides compositions for detecting biomarkers as well as compositions and methods useful for treating vascular diseases.

7 Claims, 7 Drawing Sheets

US 11,360,097 B2

PLATELET BIOMARKERS AND DIAGNOSTIC METHODS FOR VASCULAR DISEASES

CROSS-REFERENCE TO RELATED APPLICATIONS

This application is a 35 USC § 371 National Stage application of International Application No. PCT/US2016/061452 filed Nov. 11, 2016, now pending; which claims the benefit under 35 USC § 119(e) to U.S. Application Ser. No. 62/295,396 filed Feb. 15, 2016 and U.S. Application Ser. No. 62/254,184, filed on Nov. 12, 2015. The disclosure of each of the prior applications is considered part of and is incorporated by reference in the disclosure of this application.

FIELD OF THE INVENTION

The present invention relates to platelet biomarkers and diagnostic and prognostic methods for vascular diseases, including cardiovascular and cerebrovascular diseases. The invention also provides compositions for detecting platelet biomarkers (e.g., platelet-derived exosome biomarkers) as well as compositions and methods useful for treating vascular diseases.

BACKGROUND OF THE INVENTION

Human platelets constitutively generate exosomes that are secreted from endosome-derived multivesicular bodies, with lesser contributions from α-granules (Heijnen et al. (1999) Blood 94:3791-3799; Aatonen et al. (2014) J. Extracell. Vesicles 3). The release of exosomes and their quantities of cargo constituents increase after stimulation with thrombin, collagen or calcium ionophore. Platelet exosomal cargoes may include cytokines, chemokines, growth factors, coagulation factors, lipoproteins and other lipids, as well as diverse types of RNA ((Heijnen et al., supra; Aatonen et al., supra). Platelet exosome proteins reflect those of their platelet source, including the constitutively expressed glycoprotein GPIb, as well as GPV, GPIX (CD42a), GPVI, αIIbβ3, CD40L, tissue factor (TF), P-selectin, matrix metalloproteinase-14 (MMP-14), fibrinogen, and several growth factors (VEGF, TGFβ1 and BFGF) from activated platelets.

Interactions of platelets with endothelial cells and monocytes, which are important in the pathogenesis of atherosclerosis, are mediated in part by platelet exosomes (Lievens et al. (2011) Thromb. Haemost. 106:827-838; Kaplan et al. (2011) Hematology Am. Soc. Hematol. Educ. Program 2011:51-61; von Hundelshausen et al. (2014) Front. Physiol. 5:294). Many studies have not distinguished between total platelet microparticles and the exosome and microvesicle subsets, but it is platelet exosomes that serve as major mediators of platelet interactions with other types of cells. Preliminary findings suggest that uptake of platelet-derived exosomes by endothelial cells enhances their adhesiveness by both increasing endothelial expression of adherence proteins and decreasing endothelial generation of anti-adhesive factors (von Hundelshausen et al., supra; Rautou et al. (2011) Circ Res. 109:593-606; Lukasik et al. (2013) Platelets 24:63-70). Platelet exosomes also augment platelet adherence to monocytes and monocyte activation to an inflammatory phenotype (Lievens et al., supra; Setzer et al. (2006) Platelets 17:571-576; Mause et al. (2005) Arterioscler. Thromb. Vasc. Biol. 25:1512-1518).

There is a need in the art for biomarkers and methods for detecting platelet activation associated with pathogenesis of vascular diseases. Additionally, there is a need in the art for compositions for detecting biomarkers as well as compositions and methods useful for treating atherosclerosis and other vascular diseases. The present invention meets this need by providing accurate, noninvasive methods for detecting platelet activation. The present invention further provides novel methods, assays, kits, and compositions for diagnosing, prognosing, predicting, and treating atherosclerosis and other vascular diseases.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

The present invention is based on the discovery of biomarkers from platelet-derived exosomes that can be used to detect platelet activation associated with pathogenesis of vascular diseases, including cardiovascular and cerebrovascular diseases. These biomarkers can be used alone or in combination with one or more additional biomarkers or relevant clinical parameters in prognosis, diagnosis, or monitoring treatment of platelet activation associated with vascular diseases.

Biomarkers that can be used in the practice of the invention include, but are not limited to, platelet glycoproteins (GPs) Ib (GPIb, also CD42b), V (GPV), IX (GPIX, also CD42a), VI (GPVI), CXC chemokine ligand 4 (CXCL4), high mobility group box 1 (HMGB1), CXC chemokine ligand 7 (CXCL7), platelet derived growth factor-AA (PDGF-AA), thrombospondin type-1 (TSP-1), and integrin-linked kinase 1 (ILK-1). In one embodiment, the invention includes a biomarker panel comprising one or more biomarkers selected from the group consisting of GPIb, GPV, GPIX, GPVI, CXCL4, CXCL7, HMGB1, TF, P-selectin, CD40L, MMP-14, VEGF, TGFβ1, PDGF-AA, TSP-1, ILK-1, and bFGF.

In some embodiments, the present invention provides a method of detecting platelet activation in a subject, the method comprising: a) obtaining a biological sample comprising platelets from the subject; b) isolating platelet-derived exosomes from the biological sample; c) measuring levels of one or more biomarkers selected from the group consisting of GPIb, GPV, GPIX, GPVI, CXCL4, CXCL7, HMGB1, TF, P-selectin, CD40L, MMP-14, VEGF, TGFβ1, PDGF-AA, TSP-1, ILK-1, and bFGF for the platelet-derived exosomes; and d) comparing the levels of the one or more biomarkers for the platelet-derived exosomes to control levels of the one or more biomarkers for a control sample containing platelet-derived exosomes from unactivated platelets, wherein increased levels of the one or more biomarkers in the platelet-derived exosomes from the subject compared to the control levels indicate that the subject has platelet activation. The biological sample collected from the subject can be any bodily fluid comprising platelets or platelet-derived exosomes, including, but not limited to, whole blood, plasma, serum, lymph, amniotic fluid, and umbilical cord blood. The levels of the biomarkers may be measured for exosomes released by platelets intravascularly or ex vivo.

In some embodiments, the subject has been diagnosed with a vascular disorder or suspected of having a vascular disorder, which may include a cardiovascular disease or cerebrovascular disease such as, but not limited to, atherosclerosis, coronary artery disease, thrombosis, thrombophlebitis, embolism, infarction, stroke, transient ischemic attack (TIA), vascular dementia, senile dementia, and Alzheimer's disease. In other embodiments, the subject has an infection (e.g., severe, chronic or systemic infection), inflammation, other severe disease, or other condition putting the subject at risk of developing a vascular disorder. In other embodiments, the subject is at-risk of developing a vascular disorder, which may include a cardiovascular disease or cerebrovascular disease such as, but not limited to, atherosclerosis, coronary artery disease, thrombosis, thrombophlebitis, embolism, infarction, stroke, transient ischemic attack, vascular dementia, senile dementia, and Alzheimer's disease.

In some embodiments, isolating platelet-derived exosomes from the biological sample comprises: contacting the biological sample with an agent under conditions wherein a platelet-derived exosome present in the biological sample binds to the agent to form a platelet-derived exosome-agent complex; and isolating the platelet-derived exosome from the platelet-derived exosome-agent complex to obtain a sample containing the platelet-derived exosome, wherein the purity of the platelet-derived exosomes present in said sample is greater than the purity of the platelet-derived exosomes present in said biological sample. The agent may be an antibody that specifically binds to a platelet-derived exosome surface marker (e.g., CD42b, CD41, CD63, CD40L, CD62, CD81, or GPVI). Example 1 describes isolation of platelet-derived exosomes from a biological sample, for example, by immunoabsorption using an anti-human platelet glycoprotein Ib (CD42b) antibody specific for this constitutively expressed surface protein.

Biomarker proteins can be measured, for example, by performing immunohistochemistry, immunocytochemistry, immunofluorescence, immunoprecipitation, Western blotting, or an enzyme-linked immunosorbent assay (ELISA). In certain embodiments, the level of a biomarker is measured with an immunoassay. For example, the level of the biomarker can be measured by contacting an antibody with the biomarker, wherein the antibody specifically binds to the biomarker, or a fragment thereof containing an antigenic determinant of the biomarker. Antibodies that can be used in the practice of the invention include, but are not limited to, monoclonal antibodies, polyclonal antibodies, chimeric antibodies, recombinant fragments of antibodies, Fab fragments, Fab' fragments, F(ab')$_2$ fragments, F$_v$ fragments, or scF$_v$ fragments. In one embodiment, the method comprises measuring amounts of an in vitro complex comprising a labeled antibody bound to a platelet-derived exosome biomarker. In one aspect, the platelet-derived exosome biomarker is selected from the group consisting of GPIb, GPV, GPIX, GPVI, CXCL4, CXCL7, HMGB1, TF, P-selectin, CD40L, MMP-14, VEGF, TGFβ1, PDGF-AA, TSP-1, ILK-1, and bFGF. In some embodiments, increased levels of the biomarker GPIb, GPV, GPIX, GPVI, CXCL4, CXCL7, HMGB1, TF, P-selectin, CD40L, MMP-14, VEGF, TGFβ1, PDGF-AA, TSP-1, ILK-1, and bFGF proteins compared to reference value ranges of the biomarkers for a control subject indicate that the patient has platelet activation.

The levels of the biomarkers from platelet-derived exosomes from a subject can be compared to reference value ranges for the biomarkers found in one or more samples of platelet-derived exosomes from one or more subjects without platelet activation (e.g., control sample, healthy subject without vascular disease). Alternatively, the levels of the biomarkers from platelet-derived exosomes from a subject can be compared to reference values ranges for the biomarkers found in one or more samples of platelet-derived exosomes from one or more subjects with platelet activation (e.g., platelet activation reference sample, subject with vascular disease).

In some embodiments, the invention provides a method for monitoring the efficacy of an anti-platelet therapy for treating a vascular disorder in a patient, the method comprising: a) obtaining a first biological sample comprising platelets from the patient before the patient undergoes the therapy and a second biological sample comprising platelets after the patient undergoes the therapy; b) isolating platelet-derived exosomes from the first biological sample and the second biological sample; c) measuring levels of one or more biomarkers selected from the group consisting of GPIb, GPV, GPIX, GPVI, CXCL4, CXCL7, HMGB1, TF, P-selectin, CD40L, MMP-14, VEGF, TGFβ1, PDGF-AA, TSP-1, ILK-1, and bFGF for the platelet-derived exosomes from the first biological sample and the second biological sample; and d) comparing the levels of the one or more biomarkers for the platelet-derived exosomes from the first biological sample to the levels of the one or more biomarkers for the platelet-derived exosomes from the second biological sample, wherein decreased levels of the one or more biomarkers for the platelet-derived exosomes from the second biological sample compared to the levels of the one or more biomarkers for the platelet-derived exosomes from the first biological sample indicate that the patient is improving, and increased levels of the one or more biomarkers for the platelet-derived exosomes from the second biological sample compared to the levels of the one or more biomarkers for the platelet-derived exosomes from the first biological sample indicate that the patient is worsening or not responding to the therapy. In certain embodiments, the anti-platelet therapy comprises administering at least one drug that inhibits platelet activation selected from the group consisting of a cyclooxygenase inhibitor, an adenosine diphosphate receptor inhibitor, a phosphodiesterase inhibitor, a protease-activated receptor-1 (PAR-1) antagonist, a glycoprotein IIB/IIIA inhibitor, an adenosine reuptake inhibitor, and a thromboxane inhibitor. In one embodiment, the cyclooxygenase inhibitor is aspirin.

In other embodiments, the invention provides a method for monitoring platelet activation in a subject, the method comprising: a) measuring levels of one or more biomarkers selected from the group consisting of GPIb, GPV, GPIX, GPVI, CXCL4, CXCL7, HMGB1, TF, P-selectin, CD40L, MMP-14, VEGF, TGFβ1, PDGF-AA, TSP-1, ILK-1, and bFGF for platelet-derived exosomes from a first biological sample comprising platelets from the subject, wherein the first biological sample is obtained from the subject at a first time point; b) measuring levels of one or more biomarkers selected from the group consisting of GPIb, GPV, GPIX, GPVI, CXCL4, CXCL7, HMGB1, TF, P-selectin, CD40L, MMP-14, VEGF, TGFβ1, PDGF-AA, TSP-1, ILK-1, and bFGF for platelet-derived exosomes from a second biological sample comprising platelets from the subject, wherein the second biological sample is obtained from the subject at a second (i.e., later) time point; and c) comparing the levels of the biomarkers for platelet-derived exosomes from the first biological sample to the levels of the biomarkers for platelet-derived exosomes from the second biological sample, wherein decreased levels of the one or more biomarkers selected from the group consisting of GPIb, GPV, GPIX, GPVI, CXCL4, CXCL7, HMGB1, TF, P-selectin, CD40L, MMP-14, VEGF, TGFβ1, PDGF-AA, TSP-1, ILK-1, and bFGF for the platelet-derived exosomes from the second biological sample compared to the levels of the biomarkers in the first biological sample indicate reduced platelet activation and that the patient is improving, and increased levels of the one or more biomarkers selected from the group consisting of GPIb, GPV, GPIX, GPVI, CXCL4, CXCL7, HMGB1, TF, P-selectin, CD40L, MMP-14, VEGF, TGFβ1, PDGF-AA, TSP-1, ILK-1, and bFGF for the platelet-derived exosomes from the second biological sample compared to the levels of the biomarkers for the platelet-derived exosomes from the first biological sample indicate increased platelet activation and that the patient is worsening.

In yet other embodiments, the invention provides a method of treating a patient suspected of having platelet activation, the method comprising: a) detecting platelet activation in the patient or receiving information regarding the platelet activation status of the patient, as determined according to a method described herein; and b) administering a therapeutically effective amount of at least one drug that inhibits platelet activation to the subject if platelet activation is detected in the subject. Exemplary anti-platelet drugs include cyclooxygenase inhibitors, adenosine diphosphate receptor inhibitors, phosphodiesterase inhibitors, protease-activated receptor-1 (PAR-1) antagonists, glycoprotein IIB/IIIA inhibitors, adenosine reuptake inhibitors, and thromboxane inhibitors. In one embodiment, the patient who is identified as having platelet activation is treated with aspirin. After treatment, the method may further comprise monitoring the response of the patient to treatment.

In other embodiments, the invention provides a method comprising: providing a biological sample from a subject suspected of having a vascular disease; detecting the presence or level of at least one or more biomarkers selected from the group consisting of GPIb, GPV, GPIX, GPVI, CXCL4, CXCL7, HMGB1, TF, P-selectin, CD40L, MMP-14, VEGF, TGFβ1, PDGF-AA, TSP-1, ILK-1, and bFGF; and administering a treatment to the subject. In one embodiment, the method further comprises administering a therapeutically effective amount of at least one drug that inhibits platelet activation to the subject if increased levels of the one or more biomarkers are detected in the subject. In one embodiment, the method further comprises administering a therapeutically effective amount of at least one drug that inhibits platelet activation to the subject if decreased levels of the one or more biomarkers are detected in the subject. In some embodiments, the anti-platelet drug used in the methods of the present invention is selected from the group consisting of cyclooxygenase inhibitors, adenosine diphosphate receptor inhibitors, phosphodiesterase inhibitors, protease-activated receptor-1 (PAR-1) antagonists, glycoprotein IIB/IIIA inhibitors, adenosine reuptake inhibitors, and thromboxane inhibitors. In one embodiment, the subject is treated with aspirin. After treatment, the method may further comprise monitoring the response of the subject to treatment.

In other embodiments, the present invention provides a method of treating a subject with vascular disease, comprising: providing a biological sample from the subject; determining the level of at least one or more biomarkers selected from the list consisting of GPIb, GPV, GPIX, GPVI, CXCL4, CXCL7, HMGB1, TF, P-selectin, CD40L, MMP-14, VEGF, TGFβ1, PDGF-AA, TSP-1, ILK-1, and bFGF using at least one reagent that specifically binds to said biomarkers; and prescribing a treatment regimen based on the level of the one or more biomarkers. In some embodiments, the method further comprises isolating platelet-derived exosomes from the biological sample. In some embodiments, the vascular disease is selected from the group consisting of atherosclerosis, coronary artery disease, thrombosis, thrombophlebitis, embolism, infarction, stroke, transient ischemic attack (TIA), vascular dementia, senile dementia, and Alzheimer's disease.

In some embodiments, the invention provides a set of biomarkers for assessing platelet activation status of a subject, the set comprising one or more biomarkers selected from the group consisting of GPIb, GPV, GPIX, GPVI, CXCL4, CXCL7, HMGB1, TF, P-selectin, CD40L, MMP-14, VEGF, TGFβ1, PDGF-AA, TSP-1, ILK-1, and bFGF, wherein platelet-derived exosome levels of the biomarkers in the set are assayed; and wherein the biomarker levels of the set of biomarkers determine the platelet activation status of the subject with at least 40%, 50%, 60%, 70%, 75%, 80%, 85%, 90%, 95%, 99%, or 100% specificity.

In other embodiments, the invention provides a composition comprising at least one in vitro complex comprising a labeled antibody bound to a biomarker protein selected from the group consisting of GPIb, GPV, GPIX, GPVI, CXCL4, CXCL7, HMGB1, TF, P-selectin, CD40L, MMP-14, VEGF, TGFβ1, PDGF-AA, TSP-1, ILK-1, and bFGF, wherein said biomarker protein is extracted from platelet-derived exosomes of a subject who has been diagnosed with a vascular disorder, suspected of having a vascular disorder, or at risk of developing a vascular disorder. The antibody may be detectably labeled with any type of label, including, but not limited to, a fluorescent label, an enzyme label, a chemiluminescent label, or an isotopic label. In some embodiments, the composition is in a detection device (i.e., device capable of detecting labeled antibody). In other embodiments, the invention includes a composition comprising a first in vitro complex comprising a first labeled antibody bound to GPVI, a second in vitro complex comprising a second labeled antibody bound to CXCL4, and a third in vitro complex comprising a third labeled antibody bound to CXCL7. In another embodiment, the subject has platelet activation.

In other embodiments, the invention provides a kit for detecting or monitoring platelet activation in a subject. In some embodiments, the kit may include a container for holding a biological sample isolated from a subject who has been diagnosed or suspected of having a vascular disorder or at risk of developing a vascular disorder, at least one agent that specifically detects a biomarker; and printed instructions for reacting the agent with platelet-derived exosomes from the biological sample or a portion of the biological sample to detect the presence or amount of at least one biomarker. In other embodiments, the kit may also comprise one or more agents that specifically bind platelet-derived exosomes for use in isolating platelet-derived exosomes from a biological sample. In yet other embodiments, the kit may further comprise one or more control reference samples and reagents for performing an immunoassay. In certain embodiments, the agents may be packaged in separate containers. In some embodiments, the kit comprises agents for measuring the levels of GPIb, GPV, GPIX, GPVI, CXCL4, CXCL7, HMGB1, TF, P-selectin, CD40L, MMP-14, VEGF, TGFβ1, PDGF-AA, TSP-1, ILK-1, and bFGF. In still other embodiments, the kit may include antibodies that specifically bind to these biomarkers, for example, the kit may contain at least one of an antibody that specifically binds to GPVI, an antibody that specifically binds to CXCL4, and an antibody that specifically binds to CXCL7. In yet other embodiments, the kit further comprises an antibody that binds to a platelet-derived exosome surface marker (e.g., CD42b, CD41, CD63, CD40L, CD62, CD81, or GPVI).

In other embodiments, the invention provides a method for treating a vascular disorder, the method comprising the steps of: obtaining a biological sample from a subject suspected of having a vascular disorder, wherein the sample comprises platelets exosomes; measuring the level of one or more biomarkers selected from the group consisting of CD42b, CD41, CD63, CD40L, CD62, CD81, GPIb, GPV, GPIX, GPVI, CXCL4, CXCL7, HMGB1, TF, P-selectin, CD40L, MMP-14, VEGF, TGFβ1, PDGF-AA, TSP-1, ILK-1, and bFGF from the biological sample, wherein an altered level of the one or more biomarkers in the sample relative to the level in a control sample is indicative of a need for treatment; and administering an effective amount of an agent to the subject thereby treating the vascular disorder in the subject.

These and other embodiments of the present invention will readily occur to those of skill in the art in light of the disclosure herein, and all such embodiments are specifically contemplated.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

Figure 1:
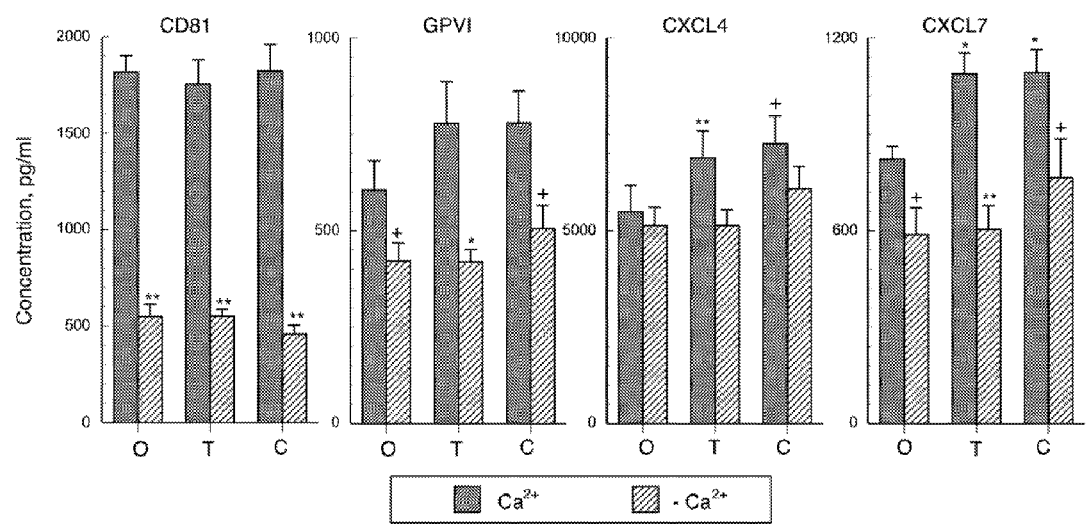
FIG. 1 sets forth data showing calcium-dependence of platelet exosome secretion and exosome protein levels. Each column and error bar depicts the mean and S.E.M. for results with platelets from six healthy subjects. Values for GPVI, CXCL4 and CXCL7 were normalized for CD81 levels in the same samples. O=no additive, T=thrombin added and C=collagen added. Statistical symbols over the dark bars show significance of difference between level with and without additive determined by a paired t test. Statistical symbols over the light bars show significance of difference between level with and without (−) $Ca^{2+}$ determined by a two-sample t test. $+P<0.05$, $*P<0.01$, $**P<0.001$.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items. It must be noted that as used herein and in the appended claims, the singular forms "a," "an," and "the" include plural references unless context clearly dictates otherwise. Thus, for example, a reference to "a fragment" includes a plurality of such fragments, a reference to an "antibody" is a reference to one or more antibodies and to equivalents thereof known to those skilled in the art, and so forth.

DESCRIPTION OF THE INVENTION

It is to be understood that the invention is not limited to the particular methodologies, protocols, cell lines, assays, and reagents described herein, as these may vary. It is also to be understood that the terminology used herein is intended to describe particular embodiments of the present invention, and is in no way intended to limit the scope of the present invention as set forth in the appended claims.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The practice of the present invention will employ, unless otherwise indicated, conventional methods of chemistry, biochemistry, molecular biology, cell biology, genetics, immunology and pharmacology, within the skill of the art. Such techniques are explained fully in the literature. See, e.g., Gennaro, A. R., ed. (1990) Remington's Pharmaceutical Sciences, 18th ed., Mack Publishing Co.; Colowick, S. et al., eds., Methods In Enzymology, Academic Press, Inc.; Handbook of Experimental Immunology, Vols. I-IV (D. M. Weir and C. C. Blackwell, eds., 1986, Blackwell Scientific Publications); Maniatis, T. et al., eds. (1989) Molecular Cloning: A Laboratory Manual, 2nd edition, Vols. I-III, Cold Spring Harbor Laboratory Press; Ausubel, F. M. et al., eds. (1999) Short Protocols in Molecular Biology, 4th edition, John Wiley & Sons; Ream et al., eds. (1998) Molecular Biology Techniques: An Intensive Laboratory Course, Academic Press); PCR (Introduction to Biotechniques Series), 2nd ed. (Newton & Graham eds., 1997, Springer Verlag).

The present invention relates, in part, to the discovery that platelet exosomal biomarkers can be used to detect platelet activation associated with pathogenesis of vascular diseases, including cardiovascular and cerebrovascular diseases. The inventor has demonstrated that increases in the platelet-derived exosome (PDE) levels of glycoprotein VI (GPVI), CXC chemokine ligand 4 (CXCL4), and CXC chemokine ligand 7 (CXCL7) are associated with activation of platelets (see Example 1).

The present invention also provides compositions for use in the methods described herein. Such compositions may include small molecule compounds; peptides and proteins including antibodies or functionally active fragments thereof.

The present invention further provides kits for detecting platelet activation in a subject, identifying a subject at risk of a vascular disorder associated with platelet activation, or prescribing a therapeutic regimen or predicting benefit from anti-platelet therapy in a subject having a vascular disorder or at risk of developing a vascular disorder. In these embodiments, the kits comprise one or more antibodies which specifically bind platelet-derived exosomes, one or more antibodies which specifically bind a biomarker, one or more containers for collecting and or holding the biological sample, and instructions for the kits use.

The section headings are used herein for organizational purposes only, and are not to be construed as in any way limiting the subject matter described herein.

Biological Sample

The present invention provides biomarkers and diagnostic and prognostic methods for vascular diseases. Biomarker levels are determined for platelet-derived exosomes from a biological sample obtained from a subject. Biological samples can include any bodily fluid comprising platelets, including, but not limited to, whole blood, plasma, serum, lymph, amniotic fluid, and umbilical cord blood.

In some embodiments, the biological sample of the invention can be obtained from blood. In some embodiments, about 1-10 mL of blood is drawn from a subject. In other embodiments, about 10-50 mL of blood is drawn from a subject. Blood can be drawn from any suitable area of the body, including an arm, a leg, or blood accessible through a central venous catheter. In some embodiments, blood is collected following a treatment or activity. For example, blood can be collected following a medical exam. The timing of collection can also be coordinated to increase the number and/or composition of platelet-derived exosomes present in the sample. For example, blood can be collected following exercise or a treatment that induces vascular dilation.

Blood may be combined with various components following collection to preserve or prepare samples for subsequent techniques. For example, in some embodiments, blood is treated with an anticoagulant, a cell fixative, a protease inhibitor, a phosphatase inhibitor, or preservative(s) for protein or DNA or RNA following collection. In some embodiments, blood is collected via venipuncture using a needle and a syringe that is emptied into collection tubes containing an anticoagulant such as EDTA, heparin, or acid citrate dextrose (ACD). Blood can also be collected using a heparin-coated syringe and hypodermic needle. Blood can also be combined with components that will be useful for cell culture. For example, in some embodiments, blood is combined with cell culture media or supplemented cell culture media (e.g., cytokines).

Enrichment or Isolation of Platelet-Derived Exosomes

Samples can be enriched for platelet-derived exosomes through positive selection, negative selection, or a combination of positive and negative selection. In some embodiments, exosomes are directly captured. In other embodiments, blood cells are captured and exosomes are collected from the remaining biological sample.

Samples can also be enriched for exosomes based on the biochemical properties of exosomes. The first step is physical isolation entailing polymer precipitation with centrifugation in one or two cycles. Then, for example, samples can be enriched for exosomes based on differences in antigens. In some of the embodiments, antibody-conjugated magnetic or paramagnetic beads in magnetic field gradients or fluorescently labeled antibodies with flow cytometry are used. In some of the embodiments based on metabolic differences, dye uptake/exclusion measured by flow cytometry or another sorting technology is used. Samples can also be enriched for exosomes based on other biochemical properties known in the art. For example, samples can be enriched for exosomes using ligands or soluble receptors.

In some embodiments, surface markers are used to positively enrich platelet-derived exosomes in the sample. In other embodiments, cell surface markers that are not found on exosomes are used to negatively enrich exosomes by depleting cell populations. Modified versions of flow cytometry sorting may also be used to further enrich for platelet-derived exosomes using surface markers or intracellular or extracellular markers conjugated to fluorescent labels. Intracellular and extracellular markers may include nuclear stains or antibodies against intracellular or extracellular proteins preferentially expressed in exosomes. Cell surface markers may include cell surface antigens that are preferentially expressed on platelet-derived exosomes. In some embodiments, the cell surface marker is a platelet-derived exosome surface marker, including, for example, CD42b, CD41, CD63, CD40L, CD62 (P-selectin), CD81, and GPVI. In some embodiments, a monoclonal antibody that specifically binds to CD42b, CD41, CD63, CD40L, CD62, CD81, GPV, GPVI or GPIX is used to enrich or isolate platelet-derived exosomes from the sample. In certain aspects, the antibody against CD42b, CD41, CD63, CD40L, CD62, CD81, GPV, GPVI or GPIX is biotinylated. In this embodiment, the biotinylated antibody can form an antibody-exosome complex that can be subsequently isolated using streptavidin-agarose resin or beads. In other embodiments, the antibody is a monoclonal anti-human CD42b, CD41, CD63, CD40L, CD62, CD81, GPV, GPVI or GPIX antibody.

In other embodiments, platelet-derived exosomes are isolated or enriched from a biological sample comprising: contacting a biological sample with an agent under conditions wherein a platelet-derived exosome present in said biological sample binds to said agent to form an exosome-agent complex; and isolating said exosome from said exosome-agent complex to obtain a sample containing said exosome, wherein the purity of the exosomes present in the sample is greater than the purity of exosomes present in the biological sample. In certain embodiments, the agent is an antibody or a lectin. Lectins useful for forming an exosome-lectin complex are described in U.S. Patent Application Publication No. 2012/0077263. In some embodiments, multiple isolating or enriching steps are performed. In certain aspects of the present embodiment, a first isolating step is performed to isolate exosomes from a blood sample freed of plasma membrane-derived membrane vesicles and a second isolating step is performed to isolate platelet-derived exosomes from other exosomes. In other embodiments, the exosome portion of the exosome-agent complex is lysed using a lysis reagent and the protein levels of the lysed exosome are assayed. In some embodiments, the antibody-exosome complex is created on a solid phase. In yet other embodiments, the methods further comprise releasing the exosome from the antibody-exosome complex. In certain embodiments, the solid phase is non-magnetic beads, magnetic beads, agarose, or sepharose. In other embodiments, the vesicle is released by exposing the antibody-exosome complex to low pH between 3.5 and 1.5. In yet other embodiments, the released exosome is neutralized by adding a high pH solution. In other embodiments, the released exosomes are lysed by incubating the released exosomes with a lysis solution. In still other embodiments, the lysis solution contains inhibitors for proteases and phosphatases.

Vascular Disorders

The present invention provides methods for detecting platelet activation associated with a vascular disorder in a subject and identifying a subject at risk of developing a vascular disorder due to platelet activation, or prescribing a therapeutic regimen or predicting benefit from anti-platelet therapy. High levels of platelet activation in vivo result in elevated platelet exosomal cargo levels of cytoadhesive, thrombogenic, and inflammatory factors, which can accelerate formation of vascular plaques, clots, and strictures. Hence, platelet activation is associated with development or worsening of a vascular disorder. Accordingly, detection of platelet activation can be used to identify individuals who will benefit from anti-platelet therapy.

In some embodiments the vascular disorder is a cardiovascular disorder or a cerebrovascular disorder such as, but not limited to, atherosclerosis, coronary artery disease, thrombosis (e.g., venous thrombosis and arterial thrombosis), thrombocytosis, thrombophlebitis, embolism (e.g., pulmonary embolism and venous thromboembolism), infarction (e.g., myocardial infarction and cerebral infarction), stroke, transient ischemic attack, myeloproliferative diseases, vascular dementia, senile dementia, and Alzheimer's disease.

Platelet activation may also be associated with an infection (e.g., severe, chronic or systemic infection), inflammation, or severe disease, which increases the risk of developing a vascular disorder. For example, platelet activation associated with sepsis, acute respiratory distress syndrome, hepatitis B virus (HBV) infection, pneumonia, or an opportunistic infection in an immunocompromised or immunodeficient patient (e.g., infected with human immunodeficiency virus (HIV)) can lead to venous thrombosis and arterial thrombosis as well as organ failure. Additionally, risk factors for developing a vascular disorder include diabetes mellitus, cigarette smoking, high blood pressure, abnormal lipid panel, increased fasting blood glucose, and a family history of premature death due to cardiovascular causes. Patients with such risk factors may benefit from testing for platelet activation by the methods described herein.

In some embodiments, the present invention enables a medical practitioner to diagnose or prognose one or more vascular disorders in a subject. In yet other embodiments, the present invention enables a medical practitioner to identify a subject at risk of developing a vascular disorder associated with platelet activation. In other embodiments, the present invention enables a medical practitioner to predict whether a subject will later develop a vascular disorder. In further embodiments the present invention enables a medical practitioner to prescribe a therapeutic regimen or predict benefit from anti-platelet therapy in a subject having a vascular disorder or at risk of developing a vascular disorder.

In certain embodiments, the subject is a mammalian subject, including, e.g., a cat, a dog, a rodent, etc. In preferred embodiments, the subject is a human subject.

Biomarkers

Platelet exosomal cargo levels of biomarker proteins are assayed for a subject having or at-risk of having a vascular disorder. In some embodiments, one or more biomarkers selected from the group consisting of GPIb, GPV, GPIX, GPVI, CXCL4, CXCL7, HMGB1, TF, P-selectin, CD40L, MMP-14, VEGF, TGFβ1, PDGF-AA, TSP-1, ILK-1, and bFGF are assayed in order to detect whether or not a subject has platelet activation. In one embodiment, all of the GPIb, GPV, GPIX, GPVI, CXCL4, CXCL7, HMGB1, TF, P-selectin, CD40L, MMP-14, VEGF, TGFβ1, PDGF-AA, TSP-1, ILK-1, and bFGF biomarkers are assayed in combination to detect platelet activation.

One of ordinary skill in the art has several methods and devices available for the detection and analysis of the biomarkers of the instant invention. With regard to polypeptides or proteins in patient test samples, immunoassay devices and methods are often used. These devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, may be employed to determine the presence or amount of analytes without the need for a labeled molecule.

Preferably the markers are analyzed using an immunoassay, although other methods are well known to those skilled in the art (for example, the measurement of marker RNA levels). The presence or amount of a marker is generally determined using antibodies specific for each marker and detecting specific binding. Any suitable immunoassay may be utilized, for example, enzyme-linked immunoassays (ELISA), radioimmunoassay (RIAs), competitive binding assays, planar waveguide technology, and the like. Specific immunological binding of the antibody to the marker can be detected directly or indirectly. Direct labels include fluorescent or luminescent tags, metals, dyes, radionuclides, and the like, attached to the antibody. Indirect labels include various enzymes well known in the art, such as alkaline phosphatase, horseradish peroxidase and the like.

The use of immobilized antibodies specific for the biomarkers is also contemplated by the present invention. The antibodies could be immobilized onto a variety of solid supports, such as magnetic or chromatographic matrix particles, the surface of an assay place (such as microtiter wells), pieces of a solid substrate material (such as plastic, nylon, paper), and the like. An assay strip could be prepared by coating the antibody or a plurality of antibodies in an array on solid support. This strip could then be dipped into the test sample and then processed quickly through washes and detection steps to generate a measurable signal, such as a colored spot.

The analysis of a plurality of biomarkers may be carried out separately or simultaneously with one test sample. Several biomarkers may be combined into one test for efficient processing of a multiple of samples. In addition, one skilled in the art would recognize the value of testing multiple samples (for example, at successive time points)

from the same individual. Such testing of serial samples will allow the identification of changes in marker levels over time. Increases or decreases in biomarker levels, as well as the absence of change in biomarker levels, would provide useful information about disease status that includes, but is not limited to the appropriateness of drug therapies (e.g., anti-platelet therapy), the effectiveness of various therapies, identification of the severity of platelet activation, and prognosis of the patient's outcome, including risk of a future vascular event.

An assay consisting of a combination of the biomarkers referenced in the instant invention may be constructed to provide relevant information related to differential diagnosis. Such a panel may be constructed using 1, 2, 3, 4, 5, 6, 7, 8, 9, 10, 15, 20, or more individual markers. The analysis of a single biomarker or subsets of biomarkers comprising a larger panel of biomarkers could be carried out using methods described within the instant invention to optimize clinical sensitivity or specificity in various clinical settings.

The analysis of markers could be carried out in a variety of physical formats as well. For example, the use of microtiter plates or automation could be used to facilitate the processing of large numbers of test samples. Alternatively, single sample formats could be developed to facilitate immediate treatment and diagnosis in a timely fashion, for example, in ambulatory transport or emergency room settings. Particularly useful physical formats comprise surfaces having a plurality of discrete, addressable locations for the detection of a plurality of different analytes. Such formats include protein microarrays, or "protein chips" and capillary devices.

Biomarkers of the present invention serve an important role in the early detection and monitoring of platelet activation associated with vascular disorders (e.g., atherosclerosis). Biomarkers are typically substances found in a bodily sample that can be measured. The measured amount can correlate with underlying disorder or disease pathophysiology (e.g., presence or absence of platelet activation) and probability of developing a vascular disorder in the future. In patients receiving treatment for their condition (e.g., anti-platelet therapy), the measured amount will also correlate with responsiveness to therapy.

In some embodiments, the biomarker is measured by a method selected from the group consisting of immunohistochemistry, immunocytochemistry, immunofluorescence, immunoprecipitation, western blotting, and ELISA.

Clinical Assay Performance

The methods of the present invention for detecting platelet activation may be used in clinical assays to diagnose or prognose a vascular disorder in a subject, identify a subject at risk of a vascular disorder, and/or for prescribing a therapeutic regimen or predicting benefit from therapy in a subject having a vascular disorder. Clinical assay performance can be assessed by determining the assay's sensitivity, specificity, area under the ROC curve (AUC), accuracy, positive predictive value (PPV), and negative predictive value (NPV). Disclosed herein are assays for diagnosing or prognosing a vascular disorder in a subject, identifying a subject at risk of a vascular disorder, or for prescribing a therapeutic regimen or predicting benefit from therapy in a subject having a vascular disorder.

The clinical performance of the assay may be based on sensitivity. The sensitivity of an assay of the present invention may be at least about 40%, 45%, 50%, 55%, 60%, 65%, 70%, 75%, 80%, 85%, 90%, 95%, 99%, or 100%. The clinical performance of the assay may be based on specificity. The specificity of an assay of the present invention may be at least about 40%, 45%, 50%, 55%, 60%, 65%, 70%, 75%, 80%, 85%, 90%, 95%, 99%, or 100%. The clinical performance of the assay may be based on area under the ROC curve (AUC). The AUC of an assay of the present invention may be at least about 0.5, 0.55, 0.6, 0.65, 0.7, 0.75, 0.8, 0.85, 0.9, or 0.95. The clinical performance of the assay may be based on accuracy. The accuracy of an assay of the present invention may be at least about 40%, 45%, 50%, 55%, 60%, 65%, 70%, 75%, 80%, 85%, 90%, 95%, 99%, or 100%.

Compositions

Compositions useful in the methods of the present invention include compositions that specifically recognize one or more biomarkers associated with platelet activation, including GPIb, GPV, GPIX, GPVI, CXCL4, CXCL7, HMGB1, TF, P-selectin, CD40L, MMP-14, VEGF, TGFβ1, PDGF-AA, TSP-1, ILK-1, and bFGF, or any combination thereof. In some embodiments, the composition enhances the activity of at least one biomarker. In other embodiments, the composition decreases the activity of at least one biomarker. In yet other embodiments, the composition comprises a peptide, a nucleic acid, an antibody, or a small molecule.

In certain embodiments, the present invention relates to compositions that specifically detect a biomarker associated with platelet activation. As detailed elsewhere herein, the present invention is based upon the finding that platelet exosomal GPIb, GPV, GPIX, GPVI, CXCL4, CXCL7, HMGB1, TF, P-selectin, CD40L, MMP-14, VEGF, TGFβ1, PDGF-AA, TSP-1, ILK-1, and bFGF proteins are specific biomarkers for platelet activation, which may be associated with atherosclerosis and other vascular disorders. In one embodiment, the compositions of the invention specifically bind to and detect one or more of the biomarkers GPIb, GPV, GPIX, GPVI, CXCL4, CXCL7, HMGB1, TF, P-selectin, CD40L, MMP-14, VEGF, TGFβ1, PDGF-AA, TSP-1, ILK-1, and bFGF, or any combination thereof. The composition of the present invention can comprise an antibody, a peptide, a small molecule, a nucleic acid, and the like.

In some embodiments, the composition comprises an antibody, wherein the antibody specifically binds to a biomarker or platelet-derived exosomes. The term "antibody" as used herein and further discussed below is intended to include fragments thereof which are also specifically reactive with a biomarker or vesicle (e.g., exosome). Antibodies can be fragmented using conventional techniques and the fragments screened for utility in the same manner as described above for whole antibodies. For example, F(ab)$_2$ fragments can be generated by treating antibody with pepsin. The resulting F(ab)$_2$ fragment can be treated to reduce disulfide bridges to produce Fab fragments. Antigen-binding portions may also be produced by recombinant DNA techniques or by enzymatic or chemical cleavage of intact antibodies. Antigen-binding portions include, inter alia, Fab, Fab', F(ab')$_2$, Fv, dAb, and complementarity determining region (CDR) fragments, single-chain antibodies (scFv), single domain antibodies, bispecific antibodies, chimeric antibodies, humanized antibodies, diabodies and polypeptides that contain at least a portion of an immunoglobulin that is sufficient to confer specific antigen binding to the polypeptide. In certain embodiments, the antibody further comprises a label attached thereto and able to be detected (e.g., the label can be a radioisotope, fluorescent compound, enzyme or enzyme co-factor).

In certain embodiments, an antibody of the invention is a monoclonal antibody, and in certain embodiments, the invention makes available methods for generating novel antibodies that specifically bind the biomarker or the exosome of the invention. For example, a method for generating a monoclonal antibody that specifically binds a biomarker or exosome, may comprise administering to a mouse an amount of an immunogenic composition comprising the biomarker or exosome, or fragment thereof, effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monocolonal antibody that binds specifically to the biomarker or exosome. Once obtained, a hybridoma can be propagated in a cell culture, optionally in culture conditions where the hybridoma-derived cells produce the monoclonal antibody that binds specifically to the biomarker or exosome. The monoclonal antibody may be purified from the cell culture.

The term "specifically reactive with" or "specifically binds" as used in reference to an antibody is intended to mean, as is generally understood in the art, that the antibody is sufficiently selective between the antigen of interest (e.g., a biomarker or exosome) and other antigens that are not of interest. In certain methods employing the antibody, such as therapeutic applications, a higher degree of specificity in binding may be desirable. Monoclonal antibodies generally have a greater tendency (as compared to polyclonal antibodies) to discriminate effectively between the desired antigens and cross-reacting polypeptides. One characteristic that influences the specificity of an antibody:antigen interaction is the affinity of the antibody for the antigen. Although the desired specificity may be reached with a range of different affinities, generally preferred antibodies will have an affinity (a dissociation constant) of about $10^{-6}$, $10^{-7}$, $10^{-8}$, $10^{-9}$ or less.

Antibodies can be generated to bind specifically to an epitope of a platelet-derived exosome or a biomarker of the present invention, including, for example, platelet-derived exosome surface markers, such as CD42b, CD41, CD63, CD40L, CD62, CD81, GPIb, GPV, GPIX, GPVI, as well as the biomarkers CXCL4, CXCL7, HMGB1, TF, MMP-14, VEGF, TGFβ1, PDGF-AA, TSP-1, ILK-1, and bFGF.

In addition, the techniques used to screen antibodies in order to identify a desirable antibody may influence the properties of the antibody obtained. A variety of different techniques are available for testing interaction between antibodies and antigens to identify particularly desirable antibodies. Such techniques include ELISAs, surface plasmon resonance binding assays (e.g., the Biacore binding assay, Biacore AB, Uppsala, Sweden), sandwich assays (e.g., the paramagnetic bead system of IGEN International, Inc., Gaithersburg, Md.), western blots, immunoprecipitation assays, immunocytochemistry, and immunohistochemistry.

In some embodiments, the present invention relates to compositions used for treating or preventing a vascular disorder. As detailed elsewhere herein, platelet activation is implicated in the pathology of a variety of vascular disorders, including cardiovascular and cerebrovascular diseases. Therefore, in one embodiment, the present invention provides compositions that inhibit platelet activation. Compositions useful for preventing and/or reducing platelet activation may include proteins, peptides, nucleic acids, small molecules, and the like.

Methods of Treatment

The present invention provides methods of treating a vascular disorder associated with platelet activation in a subject, comprising administering to the subject an effective amount of a composition, wherein the composition inhibits platelet activation. Antiplatelet therapy can be used, for example, to suppress platelet activation in a subject identified as having activated platelets by the methods of the invention. Antiplatelet drugs include, but are not limited to, cyclooxygenase inhibitors (e.g., aspirin and Triflusal (Disgren)), adenosine diphosphate (ADP) receptor inhibitors (e.g., Clopidogrel (Plavix), Prasugrel (Effient), Ticagrelor (Brilinta), and Ticlopidine (Ticlid)), phosphodiesterase inhibitors (e.g., Cilostazol (Pletal)), protease-activated receptor-1 (PAR-1) antagonists (e.g., Vorapaxar (Zontivity)), glycoprotein IIB/IIIA inhibitors (e.g., Abciximab (ReoPro), Eptifibatide (Integrilin), and Tirofiban (Aggrastat)), adenosine reuptake inhibitors (e.g., Dipyridamole (Persantine)), and thromboxane inhibitors, thromboxane synthase inhibitors and thromboxane receptor antagonists (e.g., Terutroban).

Furthermore, the methods of the invention can be used for monitoring the efficacy of antiplatelet therapy in a patient. The method comprises: analyzing the levels of one or more biomarkers selected from the group consisting of GPIb, GPV, GPIX, GPVI, CXCL4, CXCL7, HMGB1, TF, P-selectin, CD40L, MMP-14, VEGF, TGFβ1, PDGF-AA, TSP-1, ILK-1, and bFGF for platelet-derived exosomes from biological samples comprising platelets (e.g., blood) derived from the patient before and after the patient undergoes the therapy, in conjunction with respective reference levels for the biomarkers. Increasing levels of the GPIb, GPV, GPIX, GPVI, CXCL4, CXCL7, HMGB1, TF, P-selectin, CD40L, MMP-14, VEGF, TGFβ1, PDGF-AA, TSP-1, ILK-1, and bFGF exosomal biomarkers correlate with increased platelet activation and indicate that the patient is worsening or not responding to the therapy, and decreasing levels of the GPIb, GPV, GPIX, GPVI, CXCL4, CXCL7, HMGB1, TF, P-selectin, CD40L, MMP-14, VEGF, TGFβ1, PDGF-AA, TSP-1, ILK-1, and bFGF exosomal biomarkers correlate with reduced platelet activation and indicate that the condition of the patient is improving (e.g., lower risk of atherosclerosis, thrombosis, embolism, or stroke).

In some embodiments, the methods of the invention provide a method for treating a vascular disorder the method comprising the steps of: obtaining a biological sample from a subject suspected of having a vascular disorder, wherein the sample comprises platelets exosomes; measuring the level of one or more biomarkers selected from the group consisting of CD42b, CD41, CD63, CD40L, CD62, CD81, GPIb, GPV, GPIX, GPVI, CXCL4, CXCL7, HMGB1, TF, P-selectin, CD40L, MMP-14, VEGF, TGFβ1, PDGF-AA, TSP-1, ILK-1, and bFGF from the biological sample, wherein an altered level of the one or more biomarkers in the sample relative to the level in a control sample is indicative of a need for treatment; and administering an effective amount of an agent to the subject thereby treating the vascular disorder in the subject.

Kits

Another aspect of the invention encompasses kits for detecting or monitoring platelet activation in a subject. A variety of kits having different components are contemplated by the current invention. Generally speaking, the kit will include the means for quantifying one or more biomarkers in a subject. In another embodiment, the kit will include means for collecting a biological sample, means for quantifying one or more biomarkers in the biological sample, and instructions for use of the kit contents. In certain embodiments, the kit comprises a means for enriching or isolating platelet-derived exosomes in a biological sample. In further aspects, the means for enriching or isolating platelet-derived exosomes comprises reagents necessary to enrich or isolate platelet-derived exosomes from a biological sample. In certain aspects, the kit comprises a means for quantifying the amount of a biomarker. In further aspects, the means for quantifying the amount of a biomarker comprises reagents necessary to detect the amount of a biomarker.

These and other embodiments of the present invention will readily occur to those of ordinary skill in the art in view of the disclosure herein.

EXAMPLES

The invention will be further understood by reference to the following examples, which are intended to be purely exemplary of the invention. These examples are provided solely to illustrate the claimed invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description. Such modifications are intended to fall within the scope of the appended claims.

Example 1: Human Plasma Platelet-Derived Exosomes: Effects of Aspirin

Introduction

High level platelet activation in vivo elevates platelet exosomal levels of cytoadhesive, thrombogenic and inflammatory factors. Entry of such platelet exosomes into endothelial cells and perivascular macrophages augment vascular adhesiveness of platelets and monocytes, delivery of platelet and monocyte atherogenic factors to the vasculature, and development of plaques, clots and strictures in small vessels (Rautou et al. (2011) Circ Res. 109:593-606). Persistent in vivo activation of platelets may contribute through exosomal mechanisms to multiple small cerebral infarcts that lead to vascular dementia. Vascular dementia is the second most common type of senile dementia and often is a co-morbidity in Alzheimer's disease. If in vivo activation of platelets can be demonstrated convincingly in individuals who may be predisposed to cerebral infarctions, application of anti-platelet activating drugs could be justified despite the attendant increased risk of bleeding.

Methods

Characteristics of Patients and Control Subjects—

Healthy subjects, who had not ingested aspirin or other platelet-active drugs in the preceding month, signed an informed consent according to the protocol approved by the UCSF Committee for Human Research. Venous blood drawn into ACD anticoagulant was the source of platelets and platelet-poor plasma (PPP) was prepared as described (Heijnen et al. (1999) Blood 94:3791-3799; herein incorporated by reference in its entirety). Exosomes released by platelets incubated ex vivo without and with thrombin or collagen were counted by Nanosight technology and their constituents quantified by ELISAs. Platelet-derived exosomes in plasma were isolated by immunoabsorption with biotinylated mouse antihuman CD42b (platelet glycoprotein Ib) antibody plus Streptavidin Plus Ultralink resin and characterized as for exosomes derived from platelets ex vivo.

Preparation of Platelets and Platelet-Poor Plasma—

Eighteen ml of venous blood was drawn into 20 ml plastic syringes from individuals who had not ingested aspirin for at least 10 days and six ml portions were added to each of three tubes containing ACD anticoagulant solution (Vac Tube 0268429, Thermo-Fisher Scientific Co., Hanover Park, Ill.). After centrifugation at 200×g for 20 minutes at 20° C., platelet-rich plasma was transferred to a 15 ml plastic test tube containing calcium- and magnesium-free Dulbecco's balanced salt solution (DBS) (1:1, v:v) with 2 mM EDTA and PGE1 (P5515, Sigma-Aldrich, Inc., St. Louis, Mo.) at 1 µM final concentration (DBS$^{++}$). After centrifugation at 2,200×g for 20 minutes at 20° C., platelet-poor plasma (PPP) was removed and frozen in 0.5 ml aliquots at −80° C. The top of the platelet pellet was rinsed with DBS and the platelets were resuspended at 1×10$^8$ in Tyrode's buffer (NC9041478, Thermo-Fisher Scientific Co.) with 0.3 g % BSA (P137520, Thermo-Fisher Scientific Co.).

Platelet Stimulation and Exosome Isolation—

Replicate one ml platelet suspensions were supplemented with calcium chloride to a final concentration of 1 mM and incubated at 37° C. for one hour without and with 30 nM human plasma-derived thrombin (Sigma-Aldrich, Inc., 10602400001) or 50 µg/ml of human collagen (type 4 collagen from human placenta; Sigma-Aldrich, Inc., C5533-5 mg). After centrifugation at 4,000×g for 10 minutes at 4° C., supernates were transferred to new tubes, mixed with ExoQuick-TC solution (System Biosciences Co., Mountain View, Calif.) to precipitate exosomes, held at 4° C. overnight and centrifuged at 1,500×g for 30 minutes at 4° C. The exosome pellet was resuspended in 50 µL of DBS with protease inhibitor cocktail (Roche Applied Sciences, Inc., Indianapolis, Ind.) and phosphatase inhibitor cocktail (Pierce Halt, Thermo Scientific, Inc., Rockford, Ill.). After removal of 5 µL for exosome counting, 205 µL of M-PER mammalian protein extraction reagent (Thermo Scientific, Inc.) with the same inhibitor cocktails were added followed by freezing in 100 µL aliquots at −80° C.

Isolation of Platelet-Derived Exosomes from PPP—

Replicate 0.25 ml portions of PPP were incubated for 45 minutes at 20° C. with 0.1 ml of thromboplastin-D (Thermo Scientific, Inc.), received 0.15 ml of DBS with protease inhibitor and phosphatase inhibitor cocktails, and were centrifuged at 3,000×g for 15 minutes at room temperature. Exosomes were sedimented with ExoQuick solution (Systems Biosciences, Inc., Mountain View, Calif.) and re-suspended in 0.3 ml of DBS for repeat ExoQuick precipitation. This precipitate was re-suspended in 0.30 ml of distilled water:DBS (1:1, v:v) for immunochemical enrichment of exosomes. Platelet-derived exosomes were absorbed by 2 µg per suspension of biotinylated mouse anti-human CD42b (platelet glycoprotein Ib) IgG1 antibody (clone AK2, AbD Serotec, Raleigh, N.C.) for 60 minutes at 20° C. and then 10 µl of Streptavidin Plus Ultralink resin in 40 µl of 3 g % BSA (53116, Thermo Scientific, Inc.) for 60 minutes at 20° C. with gentle mixing. After centrifugation at 400×g for 5 minutes at 20° C. and removal of the supernate, exosomes were released from the immune complexes into 100 µl of 0.05 M acetic acid followed by centrifugation at 4,000×g for 10 minutes at 4° C. and transfer of the supernate into new tubes and mixing with 10 µl of Tris-HCl (pH=8.0), 25 µl of 3 g % BSA and 365 µl of M-PER solution (PI78501, Thermo Scientific, Inc.), and storage at −80° C.

Exosome Counts—

Pelleted exosomes from purified platelets and immunoprecipitated exosomes from plasmas each were diluted 1:10 to 1:200 to permit counting in the range of 10$^8$/ml to 10$^9$/ml, with an NS500 or LM10 nanoparticle tracking system (NanoSight, Amesbury, UK), as described (Fiandaca et al. (2015) Alzheimers Dement. 11(6):600-607).

ELISA Quantification of Exosome and Platelet Proteins—

All samples were quantified at a 1:1 (v:v) dilution with sample diluent from the respective ELISA kits, except for assays of PF4 that required a 1:10 to 1:20 (v:v) dilution. The sources of ELISA kits for human proteins were: platelet glycoprotein (GP) VI and CD81 (Cusabio-American Research Products, Inc., Waltham, Mass.), CXCL7 (Abcam, Inc., Cambridge, Mass.), and platelet factor 4 (PF4) and P-selectin (RayBiotech, Inc., Norcross, Ga.).

Results

Total exosome secretion by suspensions of platelets incubated in 1 µM $Ca^{2+}$-containing Tyrode's buffer was not changed by aggregation-evoking concentrations of either thrombin or collagen, as assessed by the quantities of extracted CD81 exosome marker (FIG. 1). Similarly, counts of secreted exosomes per ml in the same studies showed no differences at $5.76 \times 10^{10} \pm 0.53 \times 10^{10}$ (mean±SEM, n=6) without additive, $5.50 \times 10^{10} \pm 0.46 \times 10^{10}$ (mean±SEM) with thrombin and $5.84 \times 10^{10} \pm 0.51 \times 10^{10}$ (mean±SEM) with collagen. Platelet-derived exosomes had mean and modal diameters (±SEM) of 119±4.0 nm and 87.2±6.0 nm, respectively, that are similar to those of exosomes from other cells. The cargo of platelet-derived exosomes contained the platelet membrane marker GPVI, and platelet α-granule markers CXCL4 and CXCL7 (Kaplan et al. (1979) Blood 53:604-618). After normalization to the same amount of exosomes by the quantity of CD81, levels of α-granule proteins CXCL4 and CXCL7, but not of the membrane protein GPVI, were increased significantly by thrombin and collagen (FIG. 1). In the absence of extracellular $Ca^{2+}$, exosome secretion reflected in the levels of CD81 and the CD81-normalized levels of proteins GPVI and CXCL7, but not of CXCL4, were decreased significantly (FIG. 1). Further, the stimulatory effects of thrombin and collagen on levels of CXCL4 and CXCL7 were eliminated. Exosome counts per ml also were decreased significantly (p<0.001) without extracellular $Ca^{2+}$ to levels of $1.17 \times 10^{10} \pm 0.05 \times 10^{10}$ (mean±SEM, n=6), $1.17 \times 10^{10} \pm 0.08 \times 10^{10}$ (mean±SEM) and $1.25 \times 10^{10} \pm 0.09 \times 10^{10}$ (mean±SEM), respectively, without and with thrombin or collagen.

Figure 2:
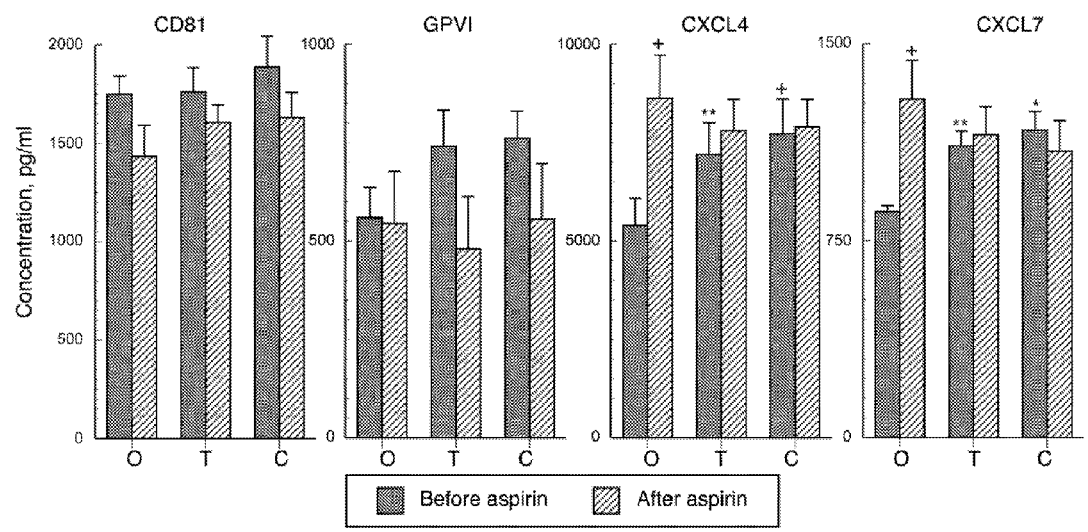
FIG. 2 sets forth data showing the effects of aspirin consumption on platelet exosome secretion and exosome cargo levels ex vivo. Column-error bar depictions, abbreviations and statistical symbols are the same as in FIG. 1; subject n=6.

Validating in vitro studies of exosome secretion by platelets from another group of six healthy subjects confirmed a lack of effect of thrombin or collagen on total exosome release assessed by CD81 content (FIG. 2, left-hand panel). Counts of secreted exosomes per ml in the same studies again showed no differences at $4.65 \times 10^{10} \pm 0.39 \times 10^{10}$ (mean±SEM, n=6) without additive, $4.88 \times 10^{10} \pm 0.27 \times 10^{10}$ (mean±SEM) with thrombin and $5.03 \times 10^{10} \pm 0.42 \times 10^{10}$ (mean±SEM) with collagen. When normalized to the same quantity of platelet exosomes by CD81 content, both thrombin and collagen again significantly increased the levels of CXCL4 and CXCL7 without altering to the same extent that of GPVI.

Consumption of low-dose aspirin daily for one week had no effect on total secretion of platelet exosomes ex vivo, as assessed by CD81 levels, nor on baseline or stimulated CD81-normalized levels of GPVI (FIG. 2). Exosome counts per ml also were not changed significantly ex vivo by aspirin consumption at levels of $4.87 \times 10^{10} \pm 0.18 \times 10^{10}$ (mean±SEM, n=6), $5.10 \times 10^{10} \pm 0.50 \times 10^{10}$ (mean±SEM) and $4.84 \times 10^{10} \pm 0.10 \times 10^{10}$ (mean±SEM), respectively, without and with thrombin or collagen. In contrast, this course of aspirin significantly elevated the baseline CD81-normalized levels of CXCL4 and CXCL7 while concurrently blocking stimulus-induced increases in their levels (FIG. 2).

Figure 3:
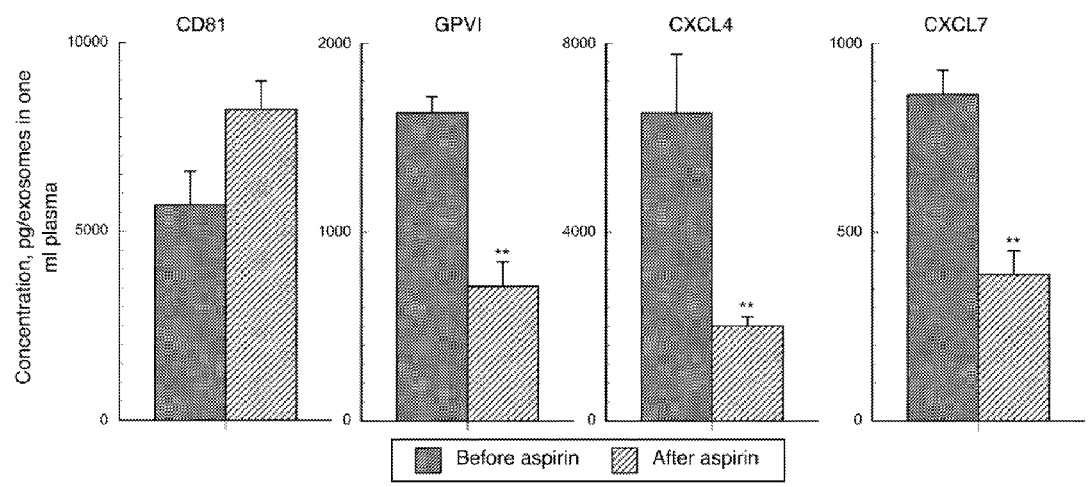
FIG. 3 sets forth data showing the effects of aspirin consumption on plasma level of platelet-derived exosomes and their cargo levels. Column-error bar depictions, abbreviations and statistical symbols are the same as in FIG. 1; subject n=6.

Intravascular generation of platelet exosomes was examined by a method developed for isolation of neuronal-derived exosomes from plasma after modification for platelet specificity (Kapogiannis et al. (2015) Faseb J. 29:589-596; et al. (2015) Alzheimers Dement. 11:600-607; Goetzl et al. (2015) Ann. Clin. Transl. Neurol. 2:769-773; Goetzl et al. (2015) Neurology 85:40-47; herein incorporated by reference). To test the immunoabsorptive effectiveness of a monoclonal antibody to a constitutively expressed platelet surface glycoprotein, exosomes secreted by $10^8$ platelets were precipitated with ExoQuick-TC polymer, resuspended and then immunoabsorbed with biotinylated mouse anti-human platelet glycoprotein Ib (CD42b) antibody plus streptavidin resin. Platelet-derived exosome recovery by immunoabsorption was a mean of 71% by levels of CD81 and, after normalization for CD81 content, the relative amounts of the three platelet biomarkers were the same as in the initial precipitate (Table 1). Platelet exosomes isolated by this same immunoabsorption technique from plasmas of six healthy subjects contained levels of the CD81 exosome marker and three platelet protein markers that were similar to those in platelet exosomes generated in vitro (FIG. 3). Plasma platelet-derived exosomes had mean and modal diameters (±SEM) of 114±13.7 nm and 84.8±11.0 nm, respectively, as for those generated ex vivo. The total level of plasma platelet exosomes, assessed by amount of CD81, was unchanged after a one-week course of low-dose aspirin, as was found for exosome secretion in vitro (FIG. 3). Exosome counts similarly were not significantly altered by aspirin, at $4.32 \times 10^{11} \pm 0.55 \times 10^{11}$ (mean±SEM, n=6) before and $3.32 \times 10^{11} \pm 0.79 \times 10^{11}$ (mean±SEM) after. Aspirin significantly suppressed the CD81-normalized levels of all platelet protein markers in vivo (p<0.001) (FIG. 3), whereas its effects in vitro were limited to the α-granule-derived proteins CXCL4 and CXCL7 (FIG. 2).

TABLE 1

Immunoabsorption of Human Platelet Exosomes

| | CD81 | GP VI | CXCL4 | CXCL7 |
|---|---|---|---|---|
| Platelet exosome precipitates | 1842 ± 214 | 478 ± 24 | 9953 ± 419 | 847 ± 22 |
| Immunopurified platelet exosomes | 1399 ± 281* | 555 ± 26 | 10685 ± 543 | 996 ± 73 |

Each value is the mean ± SEM pg/ml (n = 4) for proteins extracted from exosomes released by $10^8$ platelets into 1 ml Tyrode's buffer with 1 mM $CaCl_2$ in ½ hr at 37° C. and precipitated by ExoQuick-TC (top row) or precipitated and immunochemically purified (bottom row).
*The mean quantity of exosomal CD81 in immunopurified samples is significantly less than in preceding precipitates by a paired t test (p = 0.011). For the other three proteins, none of the differences in quantity was significant after CD81 normalization to compare for the same amount of exosomes.

Discussion

The many factors expected to regulate human platelet-derived exosome cargo loading, secretion and uptake by other intravascular cells are largely unexplored. Present results suggest differential specificity in the biochemical prerequisites and susceptibility to stimulation of exosome loading of cargo proteins (FIGS. 1 and 2). Loading of the GPVI membrane constituent and CXCL7, but not CXCL4, α-granule components as well as exosome secretion depend on extracellular calcium (FIG. 1). However, exosome loading of both CXCL4 and CXCL7, but not that of GPVI or exosome secretion, are stimulated by thrombin and collagen. The effects of aspirin consumption on platelet exosomes in vitro are restricted to modulation of loading of the α-granule chemokines CXCL4 and CXCL7 (FIG. 2). These disparate aspects of platelet exosome behavior at a minimum suggest that neither protein structure nor intraplatelet localization alone are sole determinants of biochemical regulation of cargo. Aspirin consumption reduced the in vivo loading into platelet exosomes of all three proteins examined here, which differs from the ex vivo effects of aspirin (FIGS. 2 and 3). These differences in responses to aspirin consumption of platelet exosome proteins ex vivo and in vivo indicate the likely involvement of distinctive intravascular mechanisms, which may encompass physical aspects of blood flow and additional stimuli.

Persistent in vivo activation of platelets may contribute to diverse vascular pathologies through exosomal mechanisms, either directly or by recruitment of monocyte and endothelial cell pathways (Lievens et al., supra; Rautou et al., supra; Setzer et al., supra). Cerebrovascular diseases, including multiple small cerebral infarcts that lead to vascular dementia, are the most likely vascular pathologies to involve platelet exosomes. Vascular dementia is the second most common type of senile dementia and often is a co-morbidity in Alzheimer's disease and other proteinopathic senile dementias. If in vivo activation of platelets can be demonstrated convincingly in individuals who may be predisposed to such cerebral infarctions, application of anti-platelet activation drugs could be justified despite an increased risk of bleeding.

Example 2: Human Plasma Platelet-Derived Exosomes: Effects of Aspirin

The effects of aspirin consumption on plasma levels of platelet-derived exosomes and their HMGB1 levels were determined as follows. The same methods and samples described above in Example 1 were used to determine HMGB1 levels in platelet-derived exosomes, except that a commercial ELISA kit for HMGB1 (Cusabio, American Research Products, Waltham, Mass.) was used to quantify HMGB1 levels.

As shown below in Table 2, relative amounts of HMGB1 in immunopurified platelet exosomes were similar to platelet exosomes in the initial precipitate. Platelet exosomes from plasmas of 6 healthy subjects contained HMGB1 levels that were similar to those in exosomes generated by platelets in vitro (see FIG. 3).

TABLE 2

Immunoabsorption of Human Platelet Exosomes

|  | HMGB1 |
| --- | --- |
| Platelet exosomes precipitates | 422 ± 95 |
| Immunopurified platelet exosomes | 438 ± 101 |

Each value is the mean ± SEM pg/ml (n = 4) for proteins extracted from exosomes released by $10^8$ platelets into 1 ml Tyrode's buffer with 1 mM $CaCl_2$ in ½ hr at 37° C. and precipitated by ExoQuick-TC (top row) or precipitated and immunochemically purified (bottom row).
* The mean quantity of exosomal CD81 in immunopurified samples is significantly less than in preceding precipitates by a paired t test (p = 0.011). For the other three proteins, none of the differences in quantity was significant after CD81 normalization to compare for the same amount of exosomes.

Figure 4:
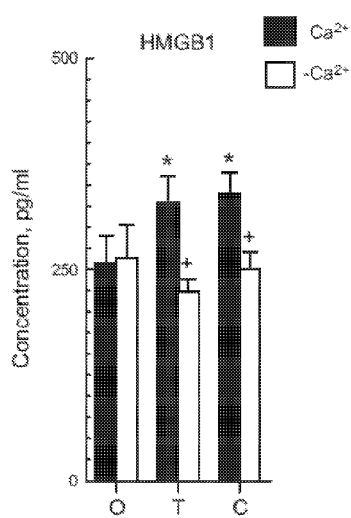
FIG. 4 sets forth data showing calcium-dependence of platelet exosome secretion and exosome HMGB1 levels. Each column and error bar depicts the mean and S.E.M. for results with platelets from six healthy subjects. Values for HMGB1 were normalized for CD81 levels in the same samples. O=no additive, T=thrombin added and C=collagen added. Statistical symbols over the dark bars show significance of difference between level with and without additive determined by a paired t test. Statistical symbols over the light bars show significance of difference between level with and without (−) $Ca^{2+}$ determined by a two-sample t test. $+P<0.05$, $*P<0.01$, $**P<0.001$.

In the in vitro studies, platelet exosomes levels of HMGB1 protein were increased significantly by thrombin and collagen (FIG. 4). Platelet exosomes levels of HMGB1 protein were unchanged in the absence of extracellular $Ca^{2+}$ (FIG. 4). The stimulatory effects of thrombin and collagen on HMGB1 levels were eliminated without $Ca^{2+}$ FIG. 4).

Figure 5:
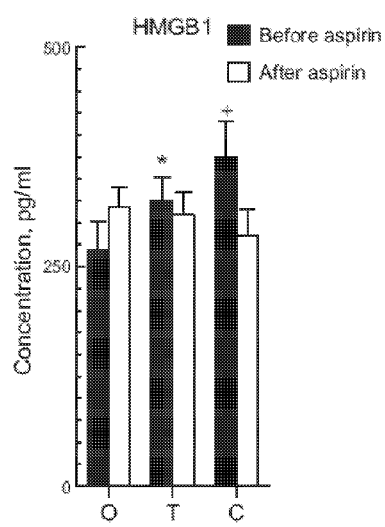
FIG. 5 sets forth data showing the effects of aspirin consumption on platelet exosome secretion and exosome HMGB1 levels ex vivo. Column-error bar depictions, abbreviations and statistical symbols are the same as in FIG. 4; subject n=6.

In the ex vivo studies, platelet exosomes levels of HMGB1 protein were increased significantly by thrombin and collagen (FIG. 5). Platelet stimulation with thrombin and collagen increased platelet exosome levels of HMGB1 (FIG. 5). Consumption of low-dose aspirin daily for 1 week blocked stimulus-induced increases in HMGB1 levels (FIG. 5)

Figure 6:
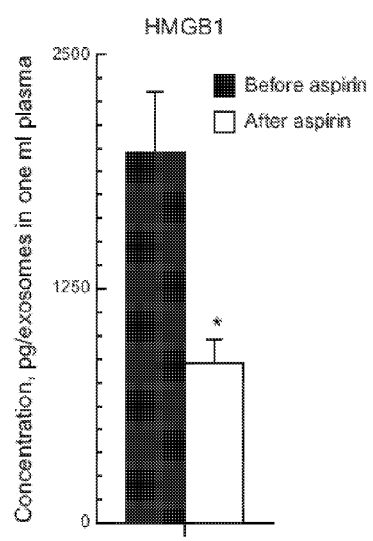
FIG. 6 sets forth data showing the effects of aspirin consumption on plasma level of platelet-derived exosomes and their HMGB1 levels. Column-error bar depictions, abbreviations and statistical symbols are the same as in FIG. 1; subject n=6.
Figure 7:
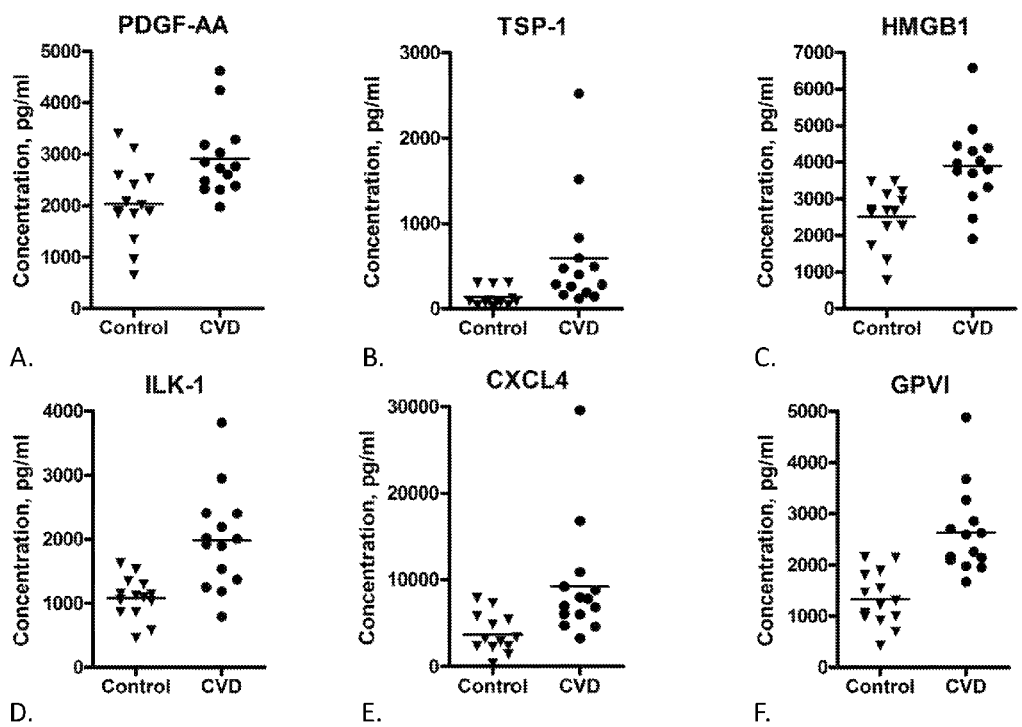
FIGS. 7A-7F set forth data showing exosomal cargo protein levels in plasma platelet-derived exosomes from subjects with cerebrovascular disease compared to normal controls.

As shown in FIG. 6, platelet exosomes from plasmas of 6 healthy subjects contained HMGB1 levels that were similar to those in exosomes generated by platelets in vitro. As shown in FIG. 6, aspirin consumption significantly reduced platelet exosomes levels of HMGB1 protein.

These results showed that aspirin can block ex vivo stimulus-induced increases in platelet-derived exosomal HMGB1 levels. These results further showed that aspirin was effective for reducing plasma exosomal levels of HMGB1 in vivo. These results demonstrated that the methods of the present invention are useful for determining protein levels in platelet-derived exosomes. These results further demonstrated that the methods of the present invention may be used to detect platelet activation associated with pathogenesis of vascular diseases, including cardiovascular and cerebrovascular diseases. The results suggested that the methods of the present invention would be useful for measuring platelet-derived exosomal protein levels for in a method of treating vascular cardiovascular and cerebrovascular diseases.

Example 3: Age Dependence of Plasma-Derived Exosomes Protein Levels

The effect of aging on plasma levels of platelet-derived exosomes protein levels was determined as follows. The methods described above in Examples 1 and 2 were used to determine protein levels in platelet-derived exosomes in plasma samples obtained from 6 healthy young subjects (age range 25-35) and 6 healthy old subjects (age range 65-75).

As shown below in Table 3, levels of total platelet exosomes in plasma were significantly lower in the older subjects, whereas protein levels normalized for the amount of CD81 were significantly higher for CXCL4, CXCL7, and HMGB1, but not GPVI, in the older subjects.

TABLE 3

Age dependence of plasma platelet exosome protein levels

| Age Range, yr | CD81 | GP VI | CXCL4 | CXCL7 | HMGB1 |
| --- | --- | --- | --- | --- | --- |
| 25-35 | 6441 ± 340 | 1616 ± 64 | 5180 ± 188 | 554 ± 35 | 1104 ± 152 |
| 65-75 | 4345 ± 310 | 1601 ± 63 | 7132 ± 131 | 837 ± 66 | 2339 ± 333 |
| P | 0.0010 | 0.87 | <0.0001 | 0.0035 | 0.0071 |

Each value is the mean ± SEM pg/ml (n = 6) for platelet-derived exosomes isolated from plasma. Values for GPVI, GXCL4, CXCL7, and HMGB1 were normalized with corresponding levels of CD81. The P values (bottom row) reflect significance of the difference between the 2 age groups.

These results showed that plasma platelet-derived exosome number is lower and its chemokine and HMGB1 levels in PDEs from thrombin-stimulated platelets was the same in CVD patients and controls (see Table 5).

TABLE 4

Levels of cargo proteins in platelet-derived exosomes (PDEs) released by ex vivo thrombin stimulation of purified platelets.

|  | PDGF-AA | GPVI | HMGB1 | ILK-1 | TSP-1 | CXCL4 |
| --- | --- | --- | --- | --- | --- | --- |
| Controls (14) | 6277 ± 806 | 1045 ± 142 | 503 ± 105 | 154 ± 33.9 | 102 ± 28.7 | 6854 ± 1287 |
| CVD patients (10) | 15595 ± 4326 | 1905 ± 374 | 1756 ± 598 | 581 ± 226 | 262 ± 52.5 | 12895 ± 1857 |
| P value | 0.0210 | 0.0245 | 0.0239 | 0.0304 | 0.0087 | 0.0118 |

All values are mean ± S.E.M. pg/ml per ng of CD81. P values were calculated with an unpaired t test.

TABLE 5

Levels of cargo proteins in platelet-derived exosomes (PDEs) isolated from plasma as a percentage of those in exosomes released from purified platelets by thrombin ex vivo.

|  | PDGF-AA | GPVI | HMGB1 | ILK-1 | TSP-1 | CXCL4 |
| --- | --- | --- | --- | --- | --- | --- |
| Controls (14) | 17.5 ± 2.74 | 77.6 ± 16.6 | 40.8 ± 8.31 | 48.7 ± 7.81 | 61.1 ± 10.1 | 8.62 ± 2.11 |
| CVD patients (10) | 22.6 ± 5.67 | 89.6 ± 18.5 | 35.6 ± 9.74 | 55.4 ± 14.7 | 49.8 ± 13.1 | 8.42 ± 2.17 |
| P value | 0.381 | 0.639 | 0.693 | 0.669 | 0.495 | 0.949 |

All values are mean ± S.E.M. for plasma PDE values as a percentage of values for PDEs released by thrombin ex vivo. P values were calculated with an unpaired t test.

higher after age 65. These results further showed that the methods of the present invention are useful for determining protein levels in platelet-derived exosomes. These results demonstrated that the methods of the present invention may be used to detect platelet activation associated with pathogenesis of vascular diseases, including cardiovascular and cerebrovascular diseases.

Example 4: Plasma-Derived Exosomes Protein Levels in Subjects with Cerebrovascular Disease Plasma levels of platelet-derived exosomes (PDEs) protein levels in subjects with cerebrovascular disease was determined as follows. The methods described above in Examples 1 and 2 were used to determine protein levels in platelet-derived exosomes in plasma samples obtained from 14 patients with documented atherosclerotic cerebrovascular disease (CVD) and one or more thrombotic strokes in the preceding 10 years, along with those from plasmas of 14 age- and gender-matched controls without CVD.

Levels of six proteins extracted from PDEs were quantified by ELISAs, including type AA platelet-derived growth factor (PDGF-AA), platelet glycoprotein VI (GPVI), high mobility group box 1 protein (HMGB1), type 1 integrin-linked kinase (ILK-1), thrombospondin-1 (TSP-1) and platelet factor 4 (chemokine CXCL4).

As shown in FIG. 1, the levels of all six proteins extracted from purified plasma PDEs were significantly higher for CVD patients than controls (see FIG. 1).

In another series of experiments, levels of exosome cargo proteins in platelet-derived exosomes (PDEs) released ex vivo from purified platelets stimulated with thrombin were determined. The methods described above in Example 1 were used to determine protein levels in PDEs released ex vivo from purified platelets stimulated with thrombin. As shown below in Table 4, levels of all six proteins extracted from PDEs released ex vivo from purified platelets stimulated with thrombin were significantly higher for CVD patients than controls. The level of each protein in plasma PDEs expressed as a percentage of the level loaded initially These results showed that PDE levels of PDGF-AA, TSP-1, HMGB1, ILK-1, CXCL4 and GPVI are increased in subjects with cerebrovascular disease. These results further showed that methods of the present invention are useful for prognosis, diagnosis, treating or monitoring treatment of platelet activation associated with vascular diseases. These results demonstrated that the methods of the present invention may be used to detect platelet activation associated with pathogenesis of vascular diseases, including cardiovascular and cerebrovascular diseases.

Various modifications of the invention, in addition to those shown and described herein, will become apparent to those skilled in the art from the foregoing description. Such modifications are intended to fall within the scope of the appended claims.

All references cited herein are hereby incorporated by reference herein in their entirety.

What is claimed is:

1. A method comprising:
   a) obtaining a biological sample comprising platelets from a subject;
   b) isolating platelet-derived exosomes from the biological sample; and
      detecting one or more biomarkers selected from the group consisting of glycoprotein Ib (GPIb), glycoprotein V (GPV), glycoprotein IX (GPIX), glycoprotein VI (GPVI), chemokine ligand 4 (CXCL4), chemokine ligand 7 (CXCL7), high mobility group box 1 (HMGB1), tissue factor (TF), P-selectin, CD40 ligand (CD40L), matrix metalloproteinase-14 (MMP-14), vascular endothelial growth factor (VEGF), Transforming Growth Factor Beta 1 (TGFβ1), Platelet-derived growth factor AA (PDGF-AA), Thrombospondin 1 (TSP-1), Integrin-linked kinase (ILK-1), and basic fibroblast growth factor (bFGF) from the platelet-derived exosomes, wherein the platelet-derived exosomes are HMGB1+ and CD42b+ and wherein said isolating platelet-derived exosomes comprises: contacting the biological sample with an agent under conditions wherein said platelet-derived exosome present in said biological sample binds to said agent to form a platelet-derived exosome-agent complex; and isolating said platelet-derived exosome from said platelet-derived exosome-agent complex to obtain a sample containing said platelet-derived exosome, and wherein the agent is a CD42b antibody or a GPVI antibody.

2. The method of claim 1, wherein the platelet-derived exosomes are released by platelets intravascularly or ex vivo.

3. The method of claim 1, wherein the biological sample is whole blood, plasma, serum, lymph, amniotic fluid, or umbilical cord blood.

4. The method of claim 1, wherein said detecting the one or more biomarkers comprises performing immunohistochemistry, immunocytochemistry, immunofluorescence, immunoprecipitation, western blotting, or an enzyme-linked immunosorbent assay (ELISA).

5. The method of claim 1, further comprising administering a therapeutically effective amount of at least one drug that inhibits platelet activation to the subject if platelet activation is detected in the subject.

6. The method of claim 5, wherein said at least one drug that inhibits platelet activation is selected from the group consisting of a cyclooxygenase inhibitor, an adenosine diphosphate receptor inhibitor, a phosphodiesterase inhibitor, a protease-activated receptor-1 (PAR-1) antagonist, a glycoprotein IIB/IIIA inhibitor, an adenosine reuptake inhibitor, and a thromboxane inhibitor.

7. The method of claim 6, wherein the cyclooxygenase inhibitor is aspirin.

* * * * *